US012029775B2

(12) United States Patent
Morra

(10) Patent No.: US 12,029,775 B2
(45) Date of Patent: *Jul. 9, 2024

(54) COMPOSITION COMPRISING POLLEN AND/OR PISTIL EXTRACTS, PREPARATION PROCESS AND ASSOCIATED USES

(71) Applicant: SERELYS PHARMA S.A.M., Monaco (MC)

(72) Inventor: Sossio Morra, Monaco (MC)

(73) Assignee: AXEEN PHARMA S.A.R.L., Monaco (MC)

( * ) Notice: Subject to any disclaimer, the term of this patent is extended or adjusted under 35 U.S.C. 154(b) by 420 days.

This patent is subject to a terminal disclaimer.

(21) Appl. No.: 16/329,034

(22) PCT Filed: Aug. 8, 2017

(86) PCT No.: PCT/EP2017/071573
§ 371 (c)(1),
(2) Date: Feb. 27, 2019

(87) PCT Pub. No.: WO2018/041790
PCT Pub. Date: Mar. 8, 2018

(65) Prior Publication Data
US 2019/0216877 A1 Jul. 18, 2019

(30) Foreign Application Priority Data

Aug. 31, 2016 (FR) ........................ 1670480

(51) Int. Cl.
| | | |
|---|---|---|
| *A61K 36/15* | (2006.01) | |
| *A61K 9/20* | (2006.01) | |
| *A61K 9/48* | (2006.01) | |
| *A61K 31/11* | (2006.01) | |
| *A61K 31/7034* | (2006.01) | |
| *A61K 36/899* | (2006.01) | |
| *A61K 38/16* | (2006.01) | |
| *A61K 38/44* | (2006.01) | |
| *A61K 38/47* | (2006.01) | |
| *A61P 5/24* | (2006.01) | |

(52) U.S. Cl.
CPC .......... *A61K 36/899* (2013.01); *A61K 9/2068* (2013.01); *A61K 9/4875* (2013.01); *A61K 31/11* (2013.01); *A61K 31/7034* (2013.01); *A61K 36/15* (2013.01); *A61K 38/168* (2013.01); *A61K 38/44* (2013.01); *A61K 38/47* (2013.01); *A61P 5/24* (2018.01)

(58) Field of Classification Search
None
See application file for complete search history.

(56) References Cited

U.S. PATENT DOCUMENTS

| | | |
|---|---|---|
| 5,712,377 A | 1/1998 | Jaton et al. |
| 2014/0141082 A1* | 5/2014 | Gao ................ A61K 31/202 424/474 |

FOREIGN PATENT DOCUMENTS

| | | | |
|---|---|---|---|
| CN | 1123116 A | * | 5/1996 |
| CN | 101116502 A | * | 2/2008 |
| WO | 2002/17944 A1 | | 3/2002 |

OTHER PUBLICATIONS

Hasanudin (Molecules (2012), vol. 17, pp. 9697-9715).*
Winther (Current Therapeutic Research (2002), vol. 63, No. 4, pp. 344-353).*
"Basic Tools of Herbalism" (http://web.archive.org/web/20041211085720/http://earthnotes.tripod.com/basics.htm—internet archived version from Dec. 2004).*
Hellstrom (Menopause (2012), vol. 19, No. 7, pp. 825-829).*
Maskat (Int. J. Drug Dev. and Res (2014), vo. 6, No. 4, pp. 28-34).*
"Pinaceae" article: https://www.britannica.com/print/article/460780—published Dec. 2017—accessed online Sep. 2022.*
"Poaceae" article: https://www.britannica.com/print/article/465603—published Aug. 2022—accessed online Sep. 2022.*
Singh ("Maceration, Percolation and Infusion Techniques for the Extraction of Medicinal and Aromatic Plants." Extraction Technologies for Medicinal and Aromatic Plants. Handa et at eds. 2008. pp. 67-82).*
WO, International Search Report with Written Opinion; International Application No. PCT/EP2017/071573 (Jun. 11, 2017).
WO, International Search Report English Translation; International Application No. PCT/EP2017/071573 (Jun. 11, 2017).
K Winther et al., "Femal, a herbal remedy made from pollen extracts, reduces hot flushes and improves quality of life in menopausal women: a randomized, placebo-controlled, parallel study", Climacteric, Jun. 3, 2005; pp. 162-170; vol. 8, No. 2 (Abstract only).
Piotr Czuczwar et al., "The safety and tolerance of phytotherapies in menopausal medicine—a review of the literature", Przeglad Menopauzalny—Menopause review, Jan. 1, 2017; pp. 8-11; vol. 16, No. 1.
Florian M E Wagenlehner et al., "A Pollen Extract (Cernilton) in Patients with Inflammatory Chronic Prostatitis-Chronic Pelvic Pain Syndrome: A Multicentre, Randomised, Prospective, Double-Blind, Placebo-Controlled Phase 3 Study", European Urology, Jun. 3, 2009; pp. 544-551; vol. 56, No. 3 (Abstract only).

(Continued)

*Primary Examiner* — Susan Hoffman
(74) *Attorney, Agent, or Firm* — FisherBroyles, LLP; Susan M. Oiler

(57) ABSTRACT

An oral composition includes one or more extracts from a plant material selected from among pollen and/or pistils originating from plants belonging to the families of Gramineae (Poaceae) and/or Pinaceae. The extract or extracts have at least one protein or peptide derived from the protein selected from the group consisting of reticuline oxidase, endochitinase A, beta-1,3-glucanase, exopolygalacturonase, non-specific lipid-transfer protein, or any combination thereof.

16 Claims, No Drawings

(56) References Cited

OTHER PUBLICATIONS

Ito R et al., "Antiprostatic hypertrophic action of Cernitin pollen-extract (Cernilton(R))", Oyo Yakuri—Pharmacometrics, Jan. 1, 1986; pp. 1-11; vol. 31.

Hiromi, "Flower Pollen Extract and its Effect on Menopause", Aug. 23, 2005; 3 pages; Retrieved on Mar. 13, 2017 from the internet.

\* cited by examiner

COMPOSITION COMPRISING POLLEN AND/OR PISTIL EXTRACTS, PREPARATION PROCESS AND ASSOCIATED USES

CROSS-REFERENCE TO RELATED APPLICATIONS

The present invention is filed under 35 U.S.C. § 371 as the U.S. national phase of International Patent Application No. PCT/EP2017/071573, filed Aug. 28, 2017, which designated the United States and which claims the benefit of French Patent Application No. 1670480, filed Aug. 31, 2016, which is hereby incorporated in its entirety including all tables, figures, and claims.

The invention belongs to the technical field of formulations comprising a pollen extract for dietary or pharmaceutical use or use as a pharmaceutical product, dietary supplement or food supplement, health supplement, or as a medical/dietary food in oral form.

Plants have been, and continue to be, the primary source of a wide variety of medicinal compounds. For centuries, various forms of botanically derived products have been used to treat innumerable infections. Botanical products are generally found in the form of powders made from one or more plants or extracts derived from whole plants or parts of selected plants. These powders and extracts are, for the most part, complex mixtures of active biological compounds and inactive biological compounds.

In modern times, herbal medicines, although increasingly accepted in Western societies, still face specific challenges. First of all, in the opinion of many highly qualified physicians, herbal medicines lack sufficient support from scientific data in our highly technical and science-oriented society. Secondly, there is concern about which compounds of a herbal remedy are pharmaceutically effective. Moreover, the issue arises concerning the concentrations or doses of such effective pharmaceutical components of herbal remedies. In summary, traditional physicians are concerned about the lack of both qualitative and quantitative standards for medicinal plants. The lack of such standardization has also led to a reluctance on the part of some regulatory agencies to accept such botanically derived medicaments.

Since plant-based treatments, defined as herbal remedies and as biologically improved plant compositions, are derived from plants, the chemical composition of such treatments from plants varies based on a number of factors, including genetic composition, the growth conditions in which the plant is produced, as well as the conditions in which the active compounds of the plan are cultured and isolated.

Consequently, biological variants of a particular plant can be expected to produce the particular chemical compounds present in the plant in substantially varying quantities. Similarly, within the same biological variant of a plant, differences in soil, molds, and other growth conditions can significantly affect the amount of a specific chemical compound produced by the plant.

Formulations composed of pollen or pollen extract are known from the prior art. Such compositions are widely used for their positive health effects, for example in combatting problems in women caused by menopause, as immune system boosters, as inhibitors of prostate cancer cells, and much more. (Bee) pollens are currently labeled as so-called superfoods or nutritious foods, because they are rich in protein, free amino acids, carbohydrates, and traces minerals.

Pollen extracts or pollen preparations are usually consumed as a dietary supplement. They can be taken in their rudimentary form, which are pollens as such, as a powder in free or encapsulated form. Alternatively, bee pollen extracts are also available on the market. WO 2002017944 describes a formulation that is composed of two separate pollen extracts. These extracts are obtained from the cytoplasm (the inner part of the grain of pollen without its coat). Since the coat is generally a source of allergens, the use of a cytoplasmic extract has a clear advantage over natural pollen.

It has been shown that specific, standardized, purified cytoplasmic extracts of pollen have a high content of superoxide dismutase (SOD) imitators, flavonoids, tannins, and polyphenols, as well as beneficial proteins and carbohydrates. The concentration of beneficial compounds in the different extracts greatly exceeds the amount of the compounds of interest in the pollens in the raw state.

The pollen extracts described in WO 2002017944 each have their specific composition and are beneficial for various medical uses. However, the content of these extracts has been found to vary from one batch to another, and no information that would enable standardization or quality control to be performed is available to date. This is not desirable when one of the goals is to sell a pharmaceutical preparation, dietary supplement, food or health supplement, or medical/dietary foods.

The products that are currently being sold suffer from the fact that there is a lack of adequate information that would allow for quality control and the subsequent standardization of pollen-derived compositions.

It is the object of the present invention to provide a purified, standardized cytoplasmic extract of specific pollen that is optimized with a high concentration of health-enhancing agents and beneficial compounds and that is composed of specific constituents that allow for the standardization and quality control of the composition comprising the extract. The extract has no or only very limited allergenic potential.

The present invention provides an oral composition comprising one or more extracts of a plant material selected from among pollen and/or pistils from plants belonging to families of Gramineae (Poaceae) and/or Pinaceae, wherein the extract or extracts comprise at least one protein or peptide derived from said protein selected from the group of reticuline oxidase, endochitinase A, beta-1,3-glucanase, exopolygalacturonase, protein nonspecific lipid-transfer protein, or any combination thereof.

It also relates to a process for preparing an aqueous pollen and pistil extract from plant(s) preferably belonging to the family of Pinaceae and/or grass (Poaceae) that comprises the successive steps of:
  a) the aqueous extraction of pollen;
  b) the aqueous extraction of pollen and pistil;
  c) spray-drying the extracts obtained in steps a) and b);
  d) recovering the plant pollen and pistil extracts obtained in c);
wherein the temperature of the extractions is strictly less than 45° C.

It also relates to an aqueous pollen and pistil extract that can be obtained by means of the process according to the invention.

Lastly, it relates to a composition or an extract according to the invention for use:
  in the treatment of symptoms of perimenopause, postmenopause, menopause, preferably menopause in women;

in the treatment of premenstrual syndrome (PMS), preferably in the treatment of premenstrual dysphoric disorders;

in the treatment of hot flushes induced by hormone therapy in patients with cancer; and in the treatment of symptoms of andropause and discomfort related to associated hormonal imbalances in men.

The composition is particularly advantageous in that it provides a broad concentration of health-promoting agents through the use of different plant materials and plant species. Moreover, the composition is highly reproducible between different batches (in terms of quality and ingredients present), which makes quality control, standardization, batch traceability, and reproducible protein profiling possible. It thus complies with good manufacturing practices for pharmaceutical products and food supplements on the market (botanical products of pharmaceutical quality). This reproducibility also provides the guarantee that each new batch of pollen extract meets the established specifications and therefore exhibits the same physiological activity as the batches used for the clinical studies. The manufacturing process makes it possible to obtain the desired beneficial compound.

The lack of standard levels of pharmaceutically active compounds in natural botanicals has led to a reluctance on the part of healthcare providers to prescribe these products to their patients.

The present invention relates to oral compositions that comprise at least one plant pollen extract and/or plant pistil extract and in which the presence of one or more protein markers and/or peptides derived from the proteins can be detected. These protein markers are a good indication of the quality of the final composition. These markers can also be used for the standardization of the compositions.

According to the invention, the term "extraction" refers to when an advantageously environmentally friendly solvent such as water, glycerin, glycols, ethers, oils, hydroalcoholic mixtures, ethanol, and other alcohols is used on a plant raw material to extract certain compounds or molecules after possible mixing, decanting, and filtering.

The solvent can then be partially or completely removed in order to obtain an extract.

After they are collected, the pollens can be used fresh or in dried form, advantageously in dried form, and optionally sterilized.

The pollen and/or pistil extracts according to the invention can be oily and/or aqueous extracts.

The term "oily extract" refers to an extract containing liposoluble active substances obtained by extraction, for example through maceration, infusion, digestion, decoction, percolation, or also lixiviation, preferably maceration at room temperature between 15 and 27° C., of a plant raw material in an oily solvent such as an ether, a ketone, or an oil.

As non-limiting examples, the oily solvent is an ether such as diethyl ether or a ketone such as acetone.

The term "aqueous extract" is understood to refer to an extract containing water-soluble active substances obtained by extraction, for example through hydrodistillation, maceration, infusion, digestion, decoction, percolation, or also lixiviation, preferably maceration at room temperature between 15 and 40° C., of a plant raw material in an aqueous solvent, i.e., a solvent that comprises water alone or advantageously water mixed with other solvent(s) such as an alcohol, a ketone, and/or a nonionic surfactant.

As non-limiting examples, the aqueous solvent is chosen from a mixture comprising predominantly water in combination with an alcohol such as ethanol, a ketone such as acetone, and/or nonionic surfactant.

The composition used according to the invention preferably comprises an aqueous pollen and/or pistil extract, more preferably an aqueous pollen and pistil extract.

According to the invention, the oral composition comprises one or more extracts from a plant material selected from among pollen and/or pistils, preferably pollen and pistils.

The pollens that are used in the present composition preferably come from plants belonging to the families of Gramineae (Poaceae) and Pinaceae.

The Poaceae, also called Gramineae (grasses), are a family of monocotyledonous plants of the order Poales. This family, consisting of about 12,000 species in 780 genera, includes most species commonly referred to as "herbs" and "cereals." They are usually herbaceous plants, more rarely woody (bamboos).

Like all anemophilous pollen, the pollen of the Poaceae has a spherical or slightly ellipsoidal shape with reduced ornamentation. The sole aperture (or pore) is round, this being one of the criteria of the monocotyledons. Poaceae pollen is small and light. The size is of the order of 40 microns. For cereals, the size is from 60 to 100 microns.

The Pinaceae, or Abietaceae, family includes gymnosperms; it includes 220-250 species divided into 11 genera. They are trees or shrubs from temperate regions, with leaves either in the form of evergreen needles or scales, or deciduous leaves like those of larches. In this family, the native species in France are among the genera *Abies* (fir trees), *Picea* (spruces), *Larix* (European larch), and *Pinus* (pines).

The Pinaceae abundantly produce large grains of pollen whose size is generally between 40 and 100 microns. They are devoid of pores. The pollen grains of pine, fir, spruce, and cedar have two air bladders that facilitate their suspension in the air. The pollen grains of larches and Douglas fir are more or less spherical and have no air bladders.

Preferably, the plants from which the pollen and/or pistil are obtained are selected from the genera *Secale, Zea, Pinus*, and/or *Dactylis*, or a mixture thereof.

More particularly, the plants from which the pollen and/or pistil are obtained are preferably chosen from among *Secale cereale* L. (rye), *Zea mays* L. (corn), *Pinus sylvestris* L. (pine), and/or *Dactylis glomerata* L. (orchardgrass), or a mixture thereof.

Advantageously, the pollen extracts are obtained from the cytoplasm (the inner part of the grain of pollen without its coat). Since the coat is generally a source of allergens and poses an obstacle to the availability of the compounds of the cytoplasm, the use of a cytoplasmic extract has a clear advantage over the use of a natural pollen extract. Such specific, standardized, purified cytoplasmic extracts of pollen have a high content of superoxide dismutase (SOD) imitators, flavonoids, tannins, and polyphenols, as well as beneficial proteins and carbohydrates. The concentration of beneficial compounds in the different extracts is far superior to the amount of the compounds of interest in the pollens in the raw state.

Thus, although the plants of both families are known to cause allergic reactions, the extracts of the present invention have no or only very limited allergenicity, since they contain no allergens or only traces of allergens. Pollen and pistil extracts from Gramineae and Pinaceae have been shown to comprise an abundance of health-promoting components and molecules, such as SODs. Use thereof can therefore have multiple beneficial effects on discomforts, diseases, and human health in general.

The term "component of a composition" should be understood as a constituent of the composition that is made up of one or more active substances.

Therefore, more particularly, a component derived from one or more extracts is equivalent to one or more extracts per se.

Here and throughout the description, unless otherwise specified, the expression "% by weight" or "w/w" (percentage by weight) refers to the relative weight of the respective compounds in relation to the total weight of the formulation.

The term "excipient" is to be understood as referring to a natural or synthetic substance that is formulated for use with an active substance that is included in the mixture for the purpose of grouping mixtures containing active substances or conferring a therapeutic improvement to the active substance in the final dosage form, for example by facilitating the absorption of the drug or its solubility or by aiding in the manufacture of the mixture.

In this description, unless otherwise specified, it is understood that when an interval is indicated, it includes the upper and lower limits of said interval.

The composition according to the invention is characterized in that the extract or extracts comprise at least one protein or peptide derived from the protein, with the proteins being selected from the group consisting of reticuline oxidase, endochitinase A, beta-1,3-glucanase, exopolygalacturonase, nonspecific lipid-transfer protein, or any combination thereof.

According to the invention, the presence of specific protein markers or peptides derived from these protein (markers) can be confirmed in the final composition, the markers being indicative of the quality of the composition and thus being suitable for use for standardization and quality control.

In fact, the applicant has been able to demonstrate that the presence of certain tracers or markers (protein or peptide derived from the protein) made it possible to confirm the presence of certain pollen and/or pistil extracts in the final composition.

The applicant has thus been able to demonstrate that the following proteins or peptides derived from the proteins enable the following pollens and/or pistils to be traced:

the pollen allergen Sec 4 (*Secale cereale*) (Q5TIW8 and Q5TIW7), glucanendo-1,3-beta-D-glucosidase (Q1EM97) enable the presence of pollen from *Secale cereale* L. to be traced, for example;

reticuline oxidase (B6T5D7), beta-1,3-glucanase (E1AFV5), pectinesterase (B6UCK8), extensin-like protein (Q9SPM0), exopolygalacturonase (PGLR2), beta-amylase (Q9SYS1), chitinase (DOEM57) make it possible, for example, to trace the pistils and pollens of *Zea mays* L.;

the pollen allergen Lol p 4 makes it possible, for example, to trace the presence of pollen from *Dactylis glomerata* L.; and the lipid-transfer protein makes it possible, for example, to trace the presence of pollen from *Pinus sylvestris* L. and/or *Zea mays* L.

The proteins or the peptides derived from the proteins that are present in the final extracts and, in fact, in the composition according to the invention are preferably chosen from the group of reticuline oxidase, endochitinase A, beta-lactamase 1,3-glucanase, exopolygalacturonase, nonspecific lipid-transfer protein, or any combination thereof.

The extract or extracts of the composition that constitute the object of the invention advantageously comprise at least one second protein or one peptide derived from said second protein selected from among the group of the pollen allergen Lol p 4 from *Dactylis glomerata* L., the pollen allergen Sec 4 (*Secale cereale*), glucanendo-1,3-beta-D-glucosidase, beta-amylase, chitinase, or any combination thereof.

The applicant has been able to demonstrate that the absence of one or more of these markers or tracers that are specific to certain pollens and/or pistils in the extracts containing said pollens and/or pistils a priori- and, in fact, in the compositions comprising such extracts a priori—was a qualitative indicator for the products.

The absence of a specific marker of a given pollen and/or pistil thus indicates that the extract or composition does not comprise said pollen and/or pistil, or that it has been denatured, thus rendering the composition comprising at least one such degraded pollen extract and/or pistil ineffective or at least less effective.

The production of an oral composition from plant extracts often requires specific production steps such as spray-drying, granulation, etc., that may have an impact on the final composition and on its constituents, such as its proteins. Due to the specific nature of the manufacturing process (typically spray-drying), certain proteins that are present in the plant raw material are likely to lose their activity or to be lost or degraded. The inventors of the present invention have found that the use of an optimized spray-drying process (temperature difference of 50° C. between inlet and outlet temperature) prevented the denaturation of relevant target proteins. The inventors of the present invention have also found that the presence in the final composition of at least one of these proteins, or peptides derived from these proteins, from among the listed proteins ensures that the quality of the composition and extracts used in the composition are optimal and of pharmaceutical quality and that the activity of the composition is not impaired. Moreover, by providing for adequate quality control, better uniformity of the content can be ensured, which is important when treating patients for specific symptoms and/or discomforts.

In a particularly advantageous manner, the composition according to the invention comprises:
an extract of pollen from *Secale cereale* L.;
an extract of pollen from *Zea mays* L.;
an extract of pollen from *Pinus sylvestris* L.;
an extract of pollen from *Dactylis glomerata* L.; and
an extract of pistil from *Zea mays* L.

Even more advantageously, the composition according to the invention comprises:
an aqueous extract of pollen from *Secale cereale* L.;
an aqueous extract of pollen from *Zea mays* L.;
an aqueous extract of pollen from *Pinus sylvestris* L.;
an aqueous extract of pollen from *Dactylis glomerata* L.; and
an aqueous extract of pistil from *Zea mays* L.

Preferably, the composition according to the invention comprises:
45% to 90% by weight of aqueous extract of pollen from *Secale cereal* L. relative to the total weight of the extract;
1% to 35% by weight of aqueous extract of pollen from *Zea mays* L. relative to the total weight of the extract;
0.01% to 5% by weight of aqueous extract of pollen from *Pinus sylvestris* L. relative to the total weight of the extract;
3% to 30% by weight of aqueous extract of pollen from *Dactylis glomerata* L. relative to the total weight of the extract; and 0.1% to 10% by weight of aqueous extract of pistil from *Zea mays* L. relative to the total weight of the extract.

Preferably, the daily dose of the aqueous pollen and/or pistil extracts of the composition according to the present invention is between 160 mg and 480 mg, more preferably between 160 and 320 mg. This daily dose is preferably administered in 1, 2 or 3 doses (morning, noon and/or evening), for example in the form of 1, 2, 3, 4 or 6 tablets.

Thus, taking the pollen and/or pistil extracts that are preferably comprised in the composition according to the invention into account, the composition comprises at least two markers or tracers which are proteins or peptides derived from the group as described above, more preferably at least three, even more preferably at least four.

According to a more preferred variant of the present invention, the derived proteins or peptides selected from among reticuline oxidase, endochitinase A, beta-1,3-glucanase, exopolygalacturonase, and nonspecific lipid-transfer protein can be identified in the composition according to the present invention.

More preferably still, the composition that constitutes the object of the invention comprises at least two markers:
the first marker of which is beta-1,3-glucanase;
the second marker of which is the Sec 4 pollen allergen (*Secale cereale*).

Surprisingly, the applicant has in fact been able to demonstrate that the above markers are particularly sensitive and are not present in the compositions of the prior art, which are not prepared according to a reproducible process such as the process that is the object of the invention.

Thus, according to a first embodiment of the invention, the composition that is the object of the invention comprises firstly:
an extract of pollen from *Secale cereale* L.;
an extract of pollen from *Zea mays* L.;
an extract of pollen from *Pinus sylvestris* L.;
an extract of pollen from *Dactylis glomerata* L.; and
an extract of pistil from *Zea mays* L.;
and, secondly, at least the following markers:
beta-1,3-glucanase (to trace the presence of pollen from *Zea mays* L.); and
the pollen allergen Sec 4 (to trace the presence of pollen and pistils from *Secale cereale*).
according to a second embodiment of the invention, the composition that is the object of the invention comprises firstly:
an extract of pollen from *Secale cereale* L.;
an extract of pollen from *Zea mays* L.;
an extract of pollen from *Pinus sylvestris* L.;
an extract of pollen from *Dactylis glomerata* L.; and
an extract of pistil from *Zea mays* L.;
and, secondly, at least the following markers:
the pollen allergen Sec 4 (*Secale cereale*) (Q5TIW8 and Q5TIW7) and/or glucanendo-1,3-beta-D-glucosidase (Q1EM97) (to trace the presence of pollen from *Secale cereale* L.);
reticuline oxidase (B6T5D7), beta-1,3-glucanase (E1AFV5), pectinesterase (B6UCK8), extensin-like protein (Q9SPMO), exopolygalacturonase (PGLR2), beta-amylase (Q9SYS1), and/or chitinase (D0EM57) (to trace the pistils and pollens of *Zea mays* L.);
the pollen allergen Lol p 4 (to trace the presence of pollen from *Dactylis glomerata* L.); and
the lipid-transfer protein (which makes it possible, for example, to trace the presence of pollen from *Pinus sylvestris* L. and/or *Zea mays* L.).

In a particularly advantageous manner, the composition used according to the invention comprises a marker or tracer for each pollen and/or pistil that is extracted.

It is also an object of the invention to provide a process for preparing a pollen and pistil extract from plant(s) belonging to the family of the Pinaceae and/or the Poaceae that comprises the successive steps of:
a) the aqueous extraction of pollen;
b) the aqueous extraction of pollen and pistil;
c) spray-drying the extracts obtained in steps a) and b);
d) recovering the plant pollen and pistil extracts obtained in c).

The applicant has been able to demonstrate that the extraction step is particularly sensitive. For instance, the temperature of the extraction must be strictly below 45° C. Beyond this temperature, one or more markers of pollen and pistils detailed above are no longer present. The quality of the composition and/or its effectiveness are therefore not assured.

The extraction temperature should be preferably below 42° C.

The duration of the extraction step, for each of the extracts, is preferably at least 6 h, more preferably at least 10 h, even more preferably at least 12 h.

Moreover, the applicant has been able to demonstrate that separation under excessively harsh conditions degrades the extract(s). To wit, when the extraction includes separation, this must not exceed 6000 revolutions per minute (rpm), preferably 4500 rpm, even more preferably 2800 rpm.

The process developed in this manner makes it possible to ensure good traceability of the pollens and pistils used. Indeed, the applicant has been able to demonstrate that the extracts manufactured according to the processes of the prior art do not make it possible to detect the presence of one or more of the above-described markers and therefore, de facto, the presence of the set of pollen and/or pistil extracts in the composition.

The compositions of the prior art are therefore not homogeneous and do not contain, in the final composition, all the expected pollen and/or pistil extracts.

Advantageously, the process that is the object of the invention comprises additional steps of separation, filtration, and/or evaporation, making it possible to increase the concentration of the final extract or to optimize the preparation of the extract.

The process that is the object of the invention also has the following advantages:
it allows for standardization;
it has excellent reproducibility;
it reduces costs by optimizing and limiting the number of industrial operations.

It also makes it possible to trace the presence of the extracts in the composition according to the invention and thus to ensure its quality and thus its effectiveness.

The noteworthy advantages of reducing handling and costs include:
simplified planning;
optimized utilization of equipment;
reduced unproductive periods (cleaning, batch change, number of validations, etc.);
limited reference number management;
a reduction in risky operations (cleaning, weighing, work procedures, reduced validation costs, stability, simplified tablet formulation, microbiological risk, traceability, etc.).

Given the fact that the preparation process according to the invention makes it possible to obtain a pollen and/or pistil extract containing markers that cannot be identified during the use of the extract preparation process according to the prior art, another object of the invention is the production of a pollen and pistil extract preferably belonging to the family of the Pinaceae and/or Poaceae that can be obtained according to the preparation process described above.

Preferably, it relates to an aqueous extract of pollen and/or pistil from *Secale cereale* L., *Zea mays* L., *Pinus sylvestris* L., and/or *Dactylis glomerata* L. that can be obtained according to the preparation process comprising the following steps of:

a) aqueous extraction of pollen from *Secale cereale* L., *Zea mays* L., *Pinus sylvestris* L., and/or *Dactylis glomerata* L. at a temperature below 45° C. in order to obtain a first extract;

b) aqueous extraction of pollen and pistils from *Zea mays* L. at a temperature below 45° C. in order to obtain a second extract;

c) mixing the first and second extracts obtained in a) and b);

d) spray-drying the mixture obtained in c);

e) recovering pollen and pistil extracts from the mixture obtained in d).

The extraction temperature must be preferably below 42° C. for each of the extracts.

The presence of the aforementioned proteins in the final composition can be confirmed by any of the suitable methods known in the art that enable identification. According to a preferred variant, the analysis is carried out by means of mass spectrometry (MS). In a more preferred variant, the analytical method is liquid chromatography (LC) or HPLC combined with mass spectrometry (MS). Suitable techniques are LC-MS with mass peptide map or SM tandem (LC-MS/MS). Preferably, the proteins and/or the protein-derived peptides can be identified by liquid chromatography-mass spectrometry.

According to another variant, the extracts come from plant materials such as pollen and/or pistils, with the appropriate plants being selected from the following group: corn (*Zea mays* L.), rye (*Secale cereale* L.), orchardgrass (*Dactylis glomerata* L.), and pine (*Pinus sylvestris* L.), or any combination thereof. It has been found by the inventors that these plant species provide quality extracts that are very beneficial to their user when they are consumed orally.

Advantageously, the abovementioned marker proteins and/or peptides that are used to verify the quality of the product can be derived from a specific plant species. For example, a check can be performed as to whether or not the quality of the material used from a specific plant species used in the composition was of optimum quality, or if one of the origins was poor. This makes traceability possible throughout the entire production of the composition from the harvesting of the plant to the final composition.

According to another or an additional variant, the reticuline oxidase, endochitinase A, beta-1,3-glucanase, and exopolygalacturonase originate from corn (*Zea mays* L.).

According to another or an additional variant, the non-specific lipid-transfer protein is derived from pine (*Pinus sylvestris* L. and/or *Zea mays* L.).

As indicated previously, according to another preferred variant of the invention, the extracts come from plant materials from *Zea mays* L., *Secale cereale* L., *Dactylis glomerata* L., *Pinus sylvestris* L., or a mixture thereof.

Preferably, the plant material used for the extracts is freshly harvested. The pollens used for the present invention can be pollens harvested by insects (such as bee pollen) or harvested by human intervention. Bee pollen, for example, contains pollen, but also nectar and bee saliva. Pollen harvested through human intervention is free of such additional ingredients. Preferably, the pollens of the present compositions are obtained only through human intervention. This, too, enables the standardization of the final product.

The compositions according to the present invention are rich in SOD imitators, flavonoids, tannins, polyphenols, vitamins, enzymes, and trace elements and have been shown to have numerous health effects, particularly in relation to women's health. The compositions according to the present invention do not contain hormones, such as phytoestrogens.

The composition according to the present invention is also rich in amino acids. Preferably, the total amount of amino acids in the composition is at least 20 g/kg, more preferably at least 25 g/kg, such as 26.3 g/kg, for example. The latter can also serve as an additional quality control for the present composition, but is also advantageous for the users as a source of essential amino acids.

The present invention also relates to a method for producing one or more extracts comprising one or more specific purified, standardized cytoplasmic pollens from a plant material selected from pollen and/or pistils. The method comprises harvesting the plant material, i.e., pollen and/or flower pistils. In order to limit the variations in the final extracts and an external influence, the harvesting is preferably performed only through human intervention.

The plant material preferably originates from plants belonging to the Gramineae and/or Pinaceae families. More preferably, the plant material originates from plants that are selected from the group of corn (e.g., *Zea mays* L.), rye (e.g., *Secale cereale* L.), orchardgrass (e.g., *Dactylis glomerata* L.), and pine (e.g., *Pinus sylvestris* L.). The plant material is at least derived from a mixture of corn pollen (*Zea mays* L.) and rye. For other preferred compositions, reference is made to the description above, which is to be understood as being included in its entirety in this section as well. The cytoplasmic fraction is subsequently extracted from the solid fraction by adding solvent such as acetone to an aqueous medium. The solid and liquid fractions are then separated, and the solid fraction can be subjected to a second extraction if deemed desirable. The specific, standardized cytoplasmic extracts of purified pollen obtained can be mixed (different extracts from different mixtures of plant materials can be added at the same time). In a subsequent step, the extracts are dried in order to obtain a powder, for example by spray-drying.

The resulting powder is then used for the manufacture of a tablet with one or more extracts, the extracts being dried extracts as described above.

According to a first variant of the invention, the composition comprises a single extract of corn pollen (*Zea mays* L.) and rye pollen (*Secale cereale* L.).

Corn (*Zea mays* L.) and rye have been shown to enable particularly rich extracts of beneficial compounds such as antioxidants to be produced.

According to a second variant of the invention, the composition comprises a mixture of at least two extracts, with a first extract originating from corn pistil (*Zea mays* L.) and pollens selected from among corn (*Zea mays* L.), rye (*Secale cereale* L.), orchardgrass (*Dactylis glomerata* L.), pine (*Pinus sylvestris* L.), or any combination thereof, and with a second extract originating from pollen and corn pistil (*Zea mays* L.).

Preferably, the first extract originates from a mixture of at least corn pollen (*Zea mays* L.), rye pollen (*Secale cereale*

L.), orchardgrass pollen (*Dactylis glomerata* L.), pine pollen (*Pinus sylvestris* L.), and corn pistil (*Zea mays* L.).

According to a third variant of the invention, the composition comprises a first and a second extract, with the first extract originating from pollens selected from among corn (*Zea mays* L.), rye (*Secale cereale* L.), pine (*Pinus sylvestris* L.), or any combination thereof, and with a second extract originating from corn pistils (*Zea mays* L.) and pollen selected from among corn (*Zea mays* L.), rye (*Secale cereale* L.), orchardgrass (*Dactylis glomerata* L.), pine (*Pinus sylvestris* L.), or any combination thereof.

Finally, according to a fourth variant of the invention, the composition comprises a single extract originating from corn pistil (*Zea mays* L.) and pollens selected from among corn (*Zea mays* L.), rye (*Secale cereale* L.), orchardgrass (*Dactylis glomerata* L.), pine (*Pinus sylvestris* L.), or any combination thereof.

The inventors have found that the health benefits associated with the composition according to any one of the variants of the present invention, with standardized, specific purified cytoplasmic pollen extracts, of a mixture of plant materials from several plants, are greater compared to compositions that include extracts of only a single plant.

The composition that is the object of the present invention may advantageously also contain a compound derived from plants selected from among *Hypericum* sp., such as *Hypericum perforatum*, *Crocus* sp., such as *Crocus sativus*, *Lavendula* sp. (lavender), *Rhodiola* sp., such as *Rhodiola rosea*, *Echium* sp., such as *Echium amoenum*, *Verbena* sp., such as *Verbena officialis*, *Avena* sp., such as *Verbena sativa*, *Eleutherococcus* sp., such as *Eleutherococcus senticosus*, *Leonurus* sp., such as *Leonurus cardia*, and *Schisandra* sp., such as *Schisandra chinensis*.

Advantageously, the active compound is safranal and/or picro(crocin).

The concentration of safranal and/or picro(crocin) is advantageously greater than 0.001% by weight relative to the total weight of the composition, preferably between 0.001% and 10%, more preferably between 0.01% and 1%.

Safranal and/or picro(crocin) are generally found in saffron. These compounds are known to be useful in the treatment and/or prevention of depression, dysphoria, or symptoms related to these disorders.

Surprisingly, the applicant has been able to demonstrate that, by adding safranal and/or (picro)crocin to the composition according to the invention, the treatment of women suffering from premenstrual syndrome (PMS) is improved.

Premenstrual syndrome (PMS) is a set of physical and emotional symptoms that usually occur 2 to 7 days before menstruation (sometimes up to 14 days). They usually end with the arrival of menstruation or within a few days thereafter.

The most common symptoms are pronounced fatigue, sensitive and swollen breasts, swelling of the lower abdomen, headaches, and irritability. Nearly 75% of fertile women experience mild symptoms the day before or when they are menstruating, such as mild cramping of the uterus.

Such a composition is therefore particularly effective and contributes to tone and vitality, reduces fatigue, helps maintain a positive mood, and promotes comfort before and during menstruation.

20% to 30% of women have symptoms intense enough to interfere with their daily activities. Among the syndromes, premenstrual dysphoric disorder (PMDD) is a severe form of premenstrual syndrome (PMS) with psychiatric symptoms at the forefront that occurs during the last week of the luteal phase and improves at the beginning of the follicular phase. The essential characteristics of PMDD are: depressive mood, anxiety and emotional lability, as well as decreased interest in daily activities. It affects 2% to 6% of women.

The composition that is the object of the invention is advantageously useful and effective for use in the treatment of premenstrual syndrome (PMS) and, more particularly, for use in the treatment of premenstrual dysphoric disorders.

The composition according to the invention is advantageously administered in the form of a pharmaceutical product, dietary or food supplement, health supplement, or a medical/dietary food.

The composition can take any of the available forms that are known in the art, such as that of a tablet, capsule (hard or soft shell), soft gel, semi-solid, solid, powder, or liquid such as an ampoule or syrup. According to a preferred variant, the composition is a tablet, capsule, or powder.

The purified, specific, standardized cytoplasmic pollen extracts can thus be provided as a component of the compositions according to the present invention in the form of granules, powder, or in a crystalline form. This can be achieved through freeze-drying, spray-drying, cylinder-drying, or vacuum-drying of the extracts obtained. Preferably, the component is a spray-dried extract as described above or a mixture of different spray-dried extracts as described.

According to another preferred variant of the invention, the composition according to the present invention can comprise excipients selected from the group of additives, such as slip agents, binders, disintegrating agents, flavorings, softeners, lubricants, anti-adherents, sorbents, and coating agents.

In order to provide a tablet with health-enhancing aspects, the one or more extracts represent at least 40% of the total composition. Alternatively, or according to another variant, the one or more extracts are present in an amount of from 160 mg to 640 mg of the total composition. This amount provides a composition that is loaded with health-enhancing compounds derived from pollen and/or pistil.

The compositions according to the present invention have been shown to be particularly useful in the treatment of symptoms relating to hormonal influences and menopause in women. More particularly, the compositions are useful for women during perimenopause or pre-menopause (the period preceding menopause), during menopause itself, and during the period following menopause. The compositions have been shown to relieve related symptoms and discomfort.

The term "treatment" refers to the improvement, prevention, or reversal of a disease or disorder or of at least one discernible symptom thereof. It is also the improvement, prevention, or reversal of at least one measurable physical parameter related to the disease or disorder being treated that cannot necessarily be perceived by the subject. In another embodiment, the term "treatment" refers to the inhibition or slowing-down of the progression of a disease or disorder, either physically (e.g., the stabilization of a discernible symptom), physiologically (e.g., the stabilization of a physical parameter), or both. The term "treatment" also refers to the delaying of the onset of a disease or disorder. In some particular embodiments of the invention, the composition of interest is administered as a preventive measure. In this context, the term "prevention" refers to a reduction in the risk of acquiring a specified disease or disorder.

Since the quality of the composition is ensured between different batches, the compositions are shown to have superior efficacy compared to the compositions that are known in the art.

Therefore, the object of the invention is also a composition or an extract as described above for use in the treatment of the symptoms of perimenopause, postmenopa use, and/or menopause, preferably menopause.

"Treatment of symptoms of menopause" is understood to refer to the treatment of symptoms such as hot flushes, sweating, palpitations, heart problems (unusual heartbeat, cessation of heartbeat, stabbing pains in the chest), muscle aches, headaches, stress incontinence or pollakiuria, dysphoria, sexual problems (changes in sexual desire, sexual activity, and satisfaction), vaginal problems (feeling of dryness or burning in the vagina, difficulty with intercourse), joint pain, mood swings and bad moods, general depressive mood, irritability, anxiety, physical and mental impairment (general decrease in performance, faulty memory, decreased concentration, memory loss), bladder problems (difficulty urinating, increased urination, urinary incontinence), discomfort in joints and muscles (joint pain, rheumatoid complaints), edema, loss of energy, sleep problems and insomnia (difficulty falling asleep, sleeping, light sleep, early awakening) weight change, hypersensitivity.

"Treatment of the symptoms of perimenopause (or premenopause)" is understood to refer to the treatment of symptoms such as nervous tension, sadness, irritability and anxiety, breast pain, hot flushes, headaches, increased sexual desire, weight gain, fatigue, cold sweats, sleep disorders, or joint pain. Perimenopause is a transitional period preceding menopause during which the secretion of sex hormones changes. This phenomenon is linked to the depletion of the ovarian follicles associated with a progressive decrease in the secretion of progesterone and estrogen. It lasts a few years and begins in women aged between 40 and 45 years old.

"Treatment of the symptoms of postmenopause" is understood to include the treatment of symptoms such as dizziness, dryness, and vaginal itching, weight gain, stress-induced incontinence, bone loss, urinary tract infections, insomnia and occasional hot flushes. Postmenopa use is defined as the period following menopause. A woman is considered to be postmenopausal when she has no longer menstruated for a whole year.

As has been demonstrated by the applicant, the composition can be advantageously used for the treatment of hot flushes, sleep disorders, joint pain, change in mood (mood swings and bad moods, general depressive mood, irritability), fatigue, and/or change in libido. More preferably, the composition is used for the treatment of hot flushes.

The applicant has also been able to demonstrate that the present composition is effective when used for the treatment of hot flushes induced by hormone therapy in patients with cancer, more particularly prostate cancer or breast cancer.

Surprisingly, the applicant has also been able to demonstrate that the present composition is effective in men. Thus, according to another aspect, the present invention also relates to a composition or an extract as described above for use as a treatment for andropause problems and discomfort related to associated hormonal imbalances in men. The term "andropause" is understood to include all aspects related to changes in the hormonal balance in men, usually due to a gradual decline in testosterone. More specifically, the composition according to the present invention can be used for the treatment of hormonal imbalances or symptoms of andropause such as hot flushes, night sweating, heart disorders (unusual awareness of beats, cessation of heartbeat, racing heart, tightness of the chest), sleep disorders (difficulty falling asleep, sleeping, light sleep, waking up early), depressed mood (feeling of vagueness, decline in professional activities, decline in leisure activities, decline in social activities), anxiety (inner agitation, panic attacks), physical and mental fatigue (general decrease in performance, poor memory, decreased concentration, memory loss), sexual problems (change in sexual desire, sexual activity, and satisfaction), bladder problems (difficulty urinating, increased need to urinate, urinary incontinence), joint and muscle discomfort (pain in the joints, rheumatoid complaints), quality of life, weight change.

The invention will be described below on the basis of non-limiting examples that illustrate the invention and are not understood and cannot be interpreted as limiting the scope of the invention.

EXAMPLE 1

Oral Compositions Used According to the Present Invention

Composition A

Composition A is a tablet that comprises a spray-dried extract obtained from a mixture of corn pollen (*Zea mays* L.), rye (*Secale cereale* L.), and pine (*Pinus sylvestris* L.) in a concentration of 60% w/w of the tablet. The presence of reticuline oxidase and nonspecific lipid-transfer protein was confirmed by means of LC-MS/MS.

Composition B

Composition B is an approximately 380 mg tablet that comprises a spray-dried extract obtained from a mixture of corn (*Zea mays* L.), rye (*Secale cereale* L.), pine (*Pinus sylvestris* L.), and orchardgrass (*Dactylis glomerata* L.) pollens and corn pistils (*Zea mays* L.) that are present in an amount by weight in the 160 mg tablet. Other ingredients in the final product include microcrystalline cellulose, magnesium stearate, and coating agents, for example. Talc and shellac were used as a coating agent. The recommended daily dose is two tablets a day, to be taken in the morning or evening. The presence of reticuline oxidase, endochitinase A, beta-1,3-glucanase, exopolygalacturonase, and nonspecific lipid-transfer protein was confirmed by means of LC-MS/MS.

All the extracts are present in a concentration of between 35% and 70% w/w of the tablet (composition B).

Composition C

Composition C is a capsule containing a powder, with the powder comprising a first freeze-dried extract obtained from a mixture of corn pollen (*Zea mays* L.), corn pistil (*Zea mays* L.), rye pollen (*Secale cereale* L.), orchardgrass pollen (*Dactylis glomerata* L.), and pine pollen (*Pinus sylvestris* L.); and a second lyophilized extract comprising corn pollen (*Zea mays* L.), rye pollen (*Secale cereale* L.), and pine pollen (*Pinus sylvestris* L.). The presence of reticuline oxidase, endochitinase A, beta-1,3-glucanase, exopolygalacturonase, and nonspecific lipid-transfer protein was confirmed by means of LC-MS/MS.

EXAMPLE 2

Quality Control by LC-MS/MS Analysis of a Composition Used According to the Present Invention In the present example, a composition according to the present composition C as well as the extract leading to the final composition were subjected to a quality control according to the present invention. The composition (of the final product) comprises a spray-dried extract obtained from a mixture of corn (*Zea mays* L.), rye (*Secale cereale* L.), pine (*Pinus sylvestris* L.), and orchardgrass (*Dactylis glomerata* L.) pollens and corn pistils (*Zea mays* L.) and was subjected to solvent extraction. The resulting liquid was separated by gel electrophoresis, and the protein bands were hydrolyzed by trypsinization.

The extracts used for the composition were also subjected to gel electrophoresis and trypsinization.

In a subsequent step, samples of both the extract and the final composition were subjected to an LC-MS/MS procedure, and the data obtained was analyzed for the presence of one of the proteins reticuline oxidase, endochitinase A, beta-1,3-glucanase, exopolygalacturonase, or nonspecific lipid-transfer protein.

The presence of reticuline oxidase and nonspecific lipid-transfer protein from pine was identified in both the extract and the final composition, indicating that the final composition is of acceptable quality and that it can be marketed. The proteins and/or peptides mentioned as markers have been shown in pollen extracts used for relevant scientific studies.

EXAMPLE 3

(Bio-)Efficacy of the Compositions Used According to the Present Invention Compared to Standard Compositions In the present example, compositions that passed quality control (that is, having at least one identifiable protein as described above)—as opposed to compositions that failed the control—were used in a demonstration.

Four menopausal women (ages 51-54) with menopausal symptoms (hot flushes, insomnia, mood swings) were randomly divided into two cohorts. Cohort A included patients who have been treated with composition B according to the present invention, while cohort B included patients who have been treated with a similar composition (from a quantitative point of view) but from different suppliers (and produced using another extraction method) and for which the presence of the proteins described in the present invention could not be verified.

All patients received a dose twice daily for three months, after which an evaluation was performed. The patients to whom the composition according to the present invention was given reported a large decrease in symptoms compared to those who received the non-inventive composition.

EXAMPLE 4

Use of a Composition According to the Present Invention for the Treatment of Premenstrual Syndrome: Two Cases A 32-year-old woman who has not been pregnant for 4 years suffered from severe premenstrual syndrome, which is characterized by hot flushes, mood swings, and irritability or fits of anger, specifically seven days before menstruation. The symptoms were marked as severe. No other health problems were reported or detected. The Papanicolaou test was normal, as was the general gynecological examination.

In a first example, oral contraceptives were given for 12 months, with no success or improvement in the symptoms of premenstrual syndrome. No other medication was given.

In an attempt to avoid the use of antidepressants, composition B according to the present invention was given to the patient in tablet form (twice a day) for three months.

After three months, the patient was given a questionnaire. The questionnaire showed that the patient observed a reduction in all symptoms from a severe condition before taking the composition to a moderate or mild condition. No side effects were detected. It was decided that the patient should continue the treatment.

The second patient is a 38-year-old woman who suffered from edema, sleep deprivation, and mood swings before menstruation. She was prescribed composition B according to the present invention in tablet form (twice a day for four months). After eight weeks, the patient reported an improvement in her symptoms (less water retention, better sleep, and fewer mood swings). These results were even better after four months of treatment. The treatment was continued.

EXAMPLE 5

Use of a Composition According to the Present Invention for the Treatment of Menopause: Two Cases A 57-year-old woman who had been in menopause for six years with two children had been receiving hormone replacement therapy (HRT) for two years in order to combat her severe menopausal symptoms (hot flushes). The therapy was stopped for fear of hormonal side effects. The patient was taking medications for stage 2 hypertension (enalapril 10 mg daily) and cholesterol-lowering drugs (atorvastatin 20 mg daily). The patient also suffered from high glucose and high BMI and had been put on a strict diet and given oral antidiabetics. After stopping the HRT, the patient reported a large increase in her hot flushes, to the point where they caused insomnia.

Considering that the patient had already been menopausal for 6 years with metabolic syndrome and pronounced hot flushes, it was decided to give her the composition B according to the present invention in tablet form twice a day for three months.

After three months of administration, the patient was given a questionnaire to evaluate treatment outcomes. The patient experienced a decline in symptoms after 5 weeks of taking the composition. After three months, the number of hot flushes was reduced by half, with a clear decrease in intensity. As a result, the problems with insomnia had dissipated.

During metabolic monitoring, administration of the composition was shown to have no effect on any of the parameters. The treatment was therefore continued.

The second patient is a 54-year-old woman suffering from edema, fatigue, and mood swings caused by a menopausal transition. After having taken composition B according to the present invention in tablet form for two months, the patient reported fewer episodes of hot flushes, which were also less pronounced, along with a significant decrease in mood swings. What is more, the fatigue was less pronounced, and her mood improved.

EXAMPLE 6

Use of a Composition According to the Present Invention for the Treatment of Hot Flushes in Men: One Case A 67-year-old male undergoing treatment with hormone therapy for local and advanced prostate cancer had been suffering from intense and frequent hot flushes (6 to 10 per day), sleep problems/insomnia, and mood swings that have generally decreased his quality of life (especially in view of the demands of his professional life) since commencing hormone therapy.

The patient was given composition B according to the present invention. After three months of administration (twice a day), the patient reported a sharp reduction in the number of episodes of hot flushes, as well as in their intensity. This has improved his quality of life in general.

EXAMPLE 7

Production of a Spray-Dried Extract According to a Variant of the Present Invention The required plant material was harvested at the appropriate time and included pollen and pistils of corn (*Zea mays* L.), rye pollen (*Secale cereale* L.), orchardgrass (*Dactylis glomerata* L.), and pine (*Pinus sylvestris* L.).

The appropriate harvesting period is:
June-July for rye pollen (*Secale cereale* L.) and orchardgrass pollen (*Dactylis glomerata* L.);
July-September for pollen and corn pistil (*Zea mays* L.); and
May-June for pine pollen (*Pinus sylvestris* L.).

This material then underwent an extraction step. The plant material was mixed with 5% acetone in an aqueous medium. The extraction took place at a temperature between 20 and 40° C. for 24 to 72 hours.

After extraction, the solid phase and the liquid phase obtained were separated by centrifugation or filtration. The liquid phase is set aside.

The resulting extract was mixed in a subsequent step and spray-dried to form a powder.

EXAMPLE 8

Qualitative and Quantitative Characterization of Pollen and Pistil Markers Contained in the Compositions According to the Invention:

a. Qualitative Characterization:

The LC-MS method was used to identify 4 species. The results of the peptide fingerprints were compared with those present in the plant protein database of sequenced organisms. To identify *Pinus sylvestris*, we performed an immunodiffusion test. The markers were chosen after the manufacture of 3 industrial batches. Among the list of proteins identified in the extract, we identified the proteins in the tablets that were "traceable," which are listed in table 1 below:

TABLE 1

| Markers or tracers associated with the species of pollen and/or pistil: | |
| --- | --- |
| Species | Proteins or peptides identified |
| Pollens from *Secale cereale* L. | Q5TIW8 - pollen allergen Sec 4 |
| | Q5TIW7 - pollen allergen Sec 4 |
| | Q1EM97 - glucanendo-1,3-beta-D-glucosidase |
| Pollens and pistils from *Zea Mays* L. | B6T5D7 - reticuline oxidase |
| | E1AFV5 - beta-13-glucanase |
| | B6UCK8 - pectinesterase |
| | Q9SPM0 - extensin-like |
| | PGLR2 - exopolygalacturonase |
| | Q9SYS1 - beta-amylase |
| | D0EM57 - chitinase |
| Pollens from *Dactylis glomerata* L. | Q5TIW3 - pollen allergen Lol p4 |
| Pollens from *Pinus sylvestris* L. | Lipid-transfer protein, positive immunological reaction | b. Quantitative Characterization: Amino Acid Titer:

Excipients for nebulization (maltodextrin, acacia) were added to the native extract. The titer of the composition ranged from 16 g/kg to 38 g/kg in total amino acids per daily dose.

EXAMPLE 9

Production of a Spray-Dried Extract According to a Variant of the Present Invention The process for preparing the extract described here is an aqueous extraction that enables controlled selection of the water-soluble proteins of interest. The chronology of the operations and the control of the manufacturing parameters make it possible to preserve specific proteins or peptides that are characteristic of the species being used. This ensures the traceability of the species in the extract. The titer of amino acids in the extract is advantageously standardized during the last stage of manufacture at the time of nebulization. By virtue of this control over the manufacturing parameters, traceability, the standardization of the amino acid titer, and intra-batch reproducibility framed by a specification of the extract are ensured.

i. Preparation of Pollen and Pistil Extracts According to the Inventive Process:

The appropriate harvesting period is:

June-July for rye pollen (*Secale cereale* L.) and orchard-grass pollen (*Dactylis glomerata* L.);

July-September for pollen and corn pistil (*Zea mays* L.); and

May-June for pine pollen (*Pinus sylvestris* L.).

The pine pollen is harvested in the wild, with the other pistils and pollen originating from agricultural crops.

The pollens and pistils are dried.

The process can be characterized by the following main steps:

a) aqueous extraction (preferably water and/or surfactant) from pollen;

b) aqueous extraction (preferably water and/or surfactant) from pollen and pistil;

c) spray-drying the extracts obtained in steps a) and b) above; and d) recovering the plant pollen and pistil extracts obtained in c).

Surprisingly, the applicant was able to identify that it was possible to increase the quality of the extracts by modifying the operating conditions of the process for preparing the extracts intended for producing the compositions according to the invention.

ii. Details of the Main Steps of the Preferred Process According to the Invention:

a. Extraction Steps:

The applicant was able to demonstrate that the temperature of the extractions should be between 30° C. and 45° C.

Preferably, the extraction is performed under continuous stirring for 12 to 90 hours.

b. Step of Spray-Drying the Mixture of Extracts:

The various extracts, preferably previously evaporated, filtered and/or decanted, are mixed in order to obtain a dry substance between 30% and 50%.

The starting temperature for the spray-drying step is from 138° C. to 168° C.

EXAMPLE 10

Comparison of Products from Two Different Processes:

A composition obtained according to the process described above (example 9) is compared with a composition obtained according to the process of the prior art, in which the extraction temperature is strictly greater than 45° C.

Both compositions comprise the following different pollens and pistils in substantially identical concentrations:

45% to 90% by weight of aqueous extract of pollen from *Secale cereal* L. relative to the total weight of the extract;

1% to 35% by weight of aqueous extract of pollen from *Zea mays* L. relative to the total weight of the extract;

0.01% to 5% by weight of aqueous extract of pollen from *Pinus sylvestris* L. relative to the total weight of the extract;

3% to 30% by weight of aqueous extract of pollen from *Dactylis glomerata* L. relative to the total weight of the extract; and 0.1% to 10% by weight of aqueous extract of pistil from *Zea mays* L. relative to the total weight of the extract.

The applicant observed that the modification of the extraction temperature and the physical separation conditions have an impact on the result of the identification tests.

The protein Q5TIW3 (pollen marker of *Dactylis glomerata* L.) is not found in the batches of extracts obtained according to the method of the prior art, whereas it is present in the batches of extracts obtained according to the process described in example 9 above.

There is no traceability of species with the old process.

The development of the process is a response to a need for traceability and reproducibility in consideration of industrial economic constraints. The search for markers/tracers in the extracts manufactured according to the old methods and those produced with the process according to the invention shows that the methods of the prior art do not enable the traceability of the species used to be ensured.

TABLE 2

Markers or tracers present in two compositions whose extracts were obtained through two different processes:

| Species | Markers from extracts obtained by means of the process according to example 9 (T° < 45° C.) | Markers from extracts obtained by means of the process according to the prior art (T° > 45° C.) |
|---|---|---|
| Pollens from *Secale cereale* L. | Q5TIW8 - pollen allergen Sec 4 | Q5TIW8 - pollen allergen Sec 4 |
| Pollens and pistils from *Zea Mays* L. | B6T5D7 - reticuline oxidase | B6T5D7 - reticuline oxidase |
| | E1AFV5 - beta-13-glucanase | E1AFV5 not identified |
| Pollens from *Dactylis glomerata* L. | Q5TIW3 - pollen allergen Lol p4 | Not identified |
| Pollens from *Pinus sylvestris* L. | Lipid-transfer protein, positive immunological reaction | Lipid-transfer protein, positive immunological reaction |

EXAMPLE 11

Additional Industrial and Qualitative Advantages Associated with the Process According to the Invention.

Advantageously, the applicant performs the extraction in a single operation. This is a simplification with industrial and qualitative advantages. This is true for the manufacture of the extract and of tablets.

In this way, the number of operations is divided by two, which saves operating time and reduces quality risks.

In terms of the extract, there is a single validation, a single weighing of the plants, a single extraction, a single control, a single cleaning, and an optimized machine occupancy time because inter-batch operations are eliminated. The quality risks of cross-contamination or weighing errors are minimized. This also applies to the microbiological risk that is part of the specification.

The reduction of quality risks makes it possible to reduce the time-consuming investigation and analysis of "out of specification" results and the possible rejection of non-compliant batches.

As such, the process that is the object of the invention offers the following particular advantages:
- improved standardization that ensures a constant titer consisting of the sum of the amino acids, the species, resulting from the extraction;
- high reproducibility: the validation of industrial batches shows that only the adjustment and monitoring of the extraction parameters make it possible to ensure this reproducibility;
- economic benefits: by reducing the number of operations and optimizing the use of industrial equipment.

EXAMPLE 12

Use of a Composition Obtained According to the Process that is the Object of the Invention for the Treatment of Hot Flushes Related to Menopause.

The composition of example 10 comprising extracts obtained according to the process that is the object of the invention was administered to approximately 1360 post-menopausal patients suffering from hot flushes.

The treatment was administered for a minimum of two months to the various patients.

The improvement in the symptoms of these patients is shown in table 3 below:

TABLE 3

Result of the multi-center menopause study:

| Patient cohort | Number of patients in MENOPAUSE by week | Patients in MENOPAUSE with hot flushes (%) | Satisfaction rate with the composition of example 10 (%) of patients treated | Efficacy of treatment with the composition of example 10 Scale from 1 to 5 1 = not very effective 5 = very effective | Duration of treatment with the composition of example 10 | Time to achieve the efficacy of treatment with the composition of example 10 |
|---|---|---|---|---|---|---|
| Cohort 1 | 20 | 5 | 100 | 3 | 3 months | 1 month |
| Cohort 2 | 20 | 50 | 50 | 3 | continuously | 12 months |
| Cohort 3 | 10 | 30 | 60 | 3 | 3 months | 6 months |
| Cohort 4 | 35 | 70 | 65 | 4 | 2 months | 2 months |
| Cohort 5 | 30 | 25 | 75 | 4 | 3 months | 2 months |
| Cohort 6 | 15 | 50 | 80 | 4 | continuously | 1.5 months |
| Cohort 7 | 10 | 50 | 60 | 4 | 6 months | 2 months |
| Cohort 8 | 30 | 80 | 70 | 4 | 2 years | 4 months |
| Cohort 9 | 20 | 50 | 40 | 4 | 3 months | 2-3 months |
| Cohort 10 | 10 | 70 | 60 | 3 | 3 months | 1.5 months |
| Cohort 11 | 15 | 70 | 68 | 4 | 3 months | 3 months |
| Cohort 12 | 20 | 30 | 30 | 3 | 3 months | 6 months |
| Cohort 13 | 20 | 50 | 70 | 4 | 6 months | 6 months |
| Cohort 14 | 10 | 70 | 100 | 3 | 3 months | 4 months |
| Cohort 15 | 7 | 50 | 50 | 4 | 6 months | 3 months |
| Cohort 16 | 4 | 4 | 50 | 4 | 12 months | 3 months |
| Cohort 17 | 4 | 90 | 50 | 3 | 3 months | 3 months |
| Cohort 18 | 20 | 10 | 60 | 4 | 2 months | 6 months |
| Cohort 19 | 5 | 60 | 80 | 4 | continuously | 6 months |
| Cohort 20 | 20 | 50 | 50 | 3 | 12 months | 6-12 months |
| Cohort 21 | 10 | 50 | 90 | 4.5 | 3 months | 2-3 months |

TABLE 3-continued

Result of the multi-center menopause study:

| Patient cohort | Number of patients in MENOPAUSE by week | Patients in MENOPAUSE with hot flushes (%) | Satisfaction rate with the composition of example 10 (%) of patients treated | Efficacy of treatment with the composition of example 10 Scale from 1 to 5 1 = not very effective 5 = very effective | Duration of treatment with the composition of example 10 | Time to achieve the efficacy of treatment with the composition of example 10 |
|---|---|---|---|---|---|---|
| Cohort 22 | 15 | 20 | 40 | 3 | 3 months | 2-3 months |
| Cohort 23 | 20 | 80 | 65 | 4 | 3 months | 3 months |
| Cohort 24 | 20 | 5 | 50 | 2.5 | 3 | 3 months |
| Cohort 25 | 25 | 70 | 85 | 4 | 3 | 1.5 months |
| Cohort 26 | 40 | 85 | 75 | 5 | continuously | 2 months |
| Cohort 27 | 10 | 90 | 95 | 5 | 3 months | 1 months |

The table above shows that patients found the treatment of hot flushes associated with menopause to be particularly effective.

Its efficacy is felt very quickly. It manifests itself primarily in the reduction of the number, frequency, and duration of hot flushes.

Moreover, some patients spontaneously reported improvement in other symptoms related to menopause, such as:

mood disorders or irritability;
sleep disorders, insomnia, or fatigue;
joint pain; and
disorders of the libido.

The physicians also reported that the tolerance to the treatment was excellent and that they observed no side effects.

EXAMPLE 13

Use of a Composition Obtained According to the Process that is the Object of the Invention for the Treatment of Hot Flushes Induced by Hormone Therapy in Patients Having Prostate Cancer.

The composition of example 10 comprising extracts obtained according to the process that is the object of the invention was administered to approximately 130 patients (males) with prostate cancer suffering from hot flushes induced by hormone therapy.

The treatment was administered for a minimum of two months to the various patients.

The improvement in the symptoms of these patients is shown in table 4 below:

TABLE 4

Result of the multi-center study on hormone therapy related to prostate cancer:

| Patient cohort | Number of patients with prostate cancer | Patients suffering from hot flushes (%) | Hot flushes (HF) induced by hormone therapy | Satisfaction rate for HF with the composition of example 10 (%) of patients treated | Time to achieve the efficacy of treatment for HF with the composition of example 10 |
|---|---|---|---|---|---|
| Cohort 1 | 7 | 40 | YES | 50% | not disclosed |
| Cohort 3 | 6 | 50 | YES | 40% | 6 months |
| Cohort 4 | 12 | 60 | YES | 100% | 2 to 3 months |
| Cohort 5 | 40 | 15 | YES | 50% | 4 weeks |
| Cohort 6 | 4 | 60 | YES | 50% | 8 weeks |
| Cohort 7 | 10 | 50 | YES | 50% | not disclosed |
| Cohort 8 | 10 | 50 | YES | 50% | 8 weeks |
| Cohort 9 | 6 | 50 | YES | 40% | 6 months |
| Cohort 10 | 7 | 40 | YES | 50% | not disclosed |
| Cohort 11 | 50 | 10 | YES | 40% | 3 weeks |
| Cohort 12 | 10 | 50 | YES | 50% | 6 weeks |
| Cohort 13 | 20 | 20 | YES | 10% | 6 weeks |
| Cohort 14 | 20 | 80 | YES | 80% | 4 weeks |
| Cohort 15 | 10 | 50 | YES | 20% | 6 weeks |
| Cohort 16 | 10 | 40 | YES | 30% | 6 weeks |
| Cohort 17 | 20 | 50 | YES | 30% | 6 weeks |
| Cohort 18 | 15 | 60 | YES | 20% | 12 weeks |
| Cohort 19 | 10 | 50 | YES | 20% | 13 weeks |
| Cohort 20 | 10 | 10 | YES | 20% | 14 weeks |
| Cohort 25 | 4 | 75 | YES | 50% | 3 weeks |
| Cohort 26 | 20 | 30 | YES | 50% | 4 weeks |
| Cohort 27 | 10 | 10 | YES | 50% | 4 weeks |

The table above shows that patients found the treatment of hot flushes induced by hormone therapy to be particularly effective.

Moreover, its efficacy is felt very quickly. It manifests itself primarily in the reduction of the number, intensity, and duration of hot flushes.

These patients' quality of life is thus improved.

The invention claimed is:

1. An oral composition comprising;
   aqueous extracts of a *Secale, Zea, Pinus sylvestris,* and *Dactylis* plant material where the plant material for each of *Secale, Zea, Pinus sylvestris,* and *Dactylis* is selected from the group consisting of cytoplasm of pollen, the inner part of the grain of pollen without a coat, and pistils collected under aqueous extraction at a temperature less than 45° C. with water mixed with a ketone, an alcohol, or a nonionic surfactant with subsequent spray drying at a starting temperature in a range of 138° C. and 168° C., wherein the aqueous extract or extracts comprise at least one protein or peptide derived from said protein, and said at least one protein comprises beta-1,3-glucanase; and
   one or more of safranal, picrocrocin, and crocin;
   wherein the composition is in the form of a tablet, capsule, or soft gel.

2. The composition according to claim 1, wherein an extract of *Secale, Zea, Pinus sylvestris,* and *Dactylis* plant material comprises:
   an extract of cytoplasm of pollen from rye (*Secale cereale* L.);
   an extract of cytoplasm of pollen from corn (*Zea mays* L.);
   an extract of cytoplasm of pollen from pine (*Pinus sylvestris* L.);
   an extract of cytoplasm of pollen from orchardgrass (*Dactylis glomerata* L.); and
   an extract of pistil from corn (*Zea mays* L.).

3. The composition according to claim 1, comprising aqueous extracts of *Zea mays* L. and *Secale cereale* L. and comprising the cytoplasm of pollen allergen Sec 4 from *Secale cereale* or one peptide derived therefrom.

4. The composition according to claim 1, wherein the aqueous extracts of *Secale, Zea, Pinus sylvestris,* and *Dactylis* plant material comprise a mixture of at least two extracts,
   with a first extract originating from;
      corn pistil (*Zea mays* L.); and
      a mixture of cytoplasm of pollens of corn (*Zea mays* L.), rye (*Secale cereale* L.), orchardgrass (*Dactylis glomerata* L.), and pine (*Pinus sylvestris* L.); and
   with a second extract originating from:
      cytoplasm of pollen and corn pistil (*Zea mays* L.).

5. The composition according to claim 1, wherein the aqueous extracts of a *Secale, Zea, Pinus sylvestris,* and *Dactylis* plant material comprise a first and a second extract,
   with the first extract originating from:
      a mixture of corn (*Zea mays* L.), rye (*Secale cereale* L.), and pine (*Pinus sylvestris* L.) cytoplasm of pollen; and
   with a second extract originating from
      corn cytoplasm of pistils (*Zea mays* L.); and
      a mixture of corn (*Zea mays* L.), rye (*Secale cereale* L.), orchardgrass (*Dactylis glomerata* L.), and pine (*Pinus sylvestris* L.) cytoplasm of pollen.

6. The composition according to claim 1, wherein the composition comprises a single extract originating from corn pistils (*Zea mays* L.) and a mixture of cytoplasm of pollens comprising corn (*Zea mays* L.), rye (*Secale cereale* L.), orchardgrass (*Dactylis glomerata* L.), and pine (*Pinus sylvestris* L.).

7. The composition of claim 1, wherein the aqueous extract comprises water in combination with an alcohol or a nonionic surfactant.

8. The composition of claim 1, wherein the aqueous extracts comprises 35% to 70% w/w of the composition.

9. The composition of claim 1, wherein the aqueous extraction is an aqueous maceration.

10. The composition of claim 9, wherein the temperature of the aqueous extraction is between 30° C. and 45° C.

11. The composition of claim 1, wherein the aqueous extraction comprises acetone.

12. A method of treating the symptoms of premenstrual syndrome (PMS) in women or perimenopause, postmenopause, or menopause in women or andropause related hormonal imbalances in men comprising:
    administering an oral composition according to claim 1 to a patient having said symptoms twice daily for at least two months;
    wherein the oral composition comprises the extract or extracts as 35% to 70% w/w of the oral composition.

13. The method of claim 12, wherein the composition comprises a mixture of at least two extracts, with a first extract originating from corn pistil (*Zea mays* L.) and cytoplasm of pollens of corn (*Zea mays* L.), rye (*Secale cereale* L.), orchardgrass (*Dactylis glomerata* L.), and pine (*Pinus sylvestris* L.), and with a second extract originating from cytoplasm of pollen and corn pistil (*Zea mays* L.).

14. The method of claim 12, wherein the composition comprises a mixture of a first and a second extract, with the first extract originating from cytoplasm of pollen selected from among corn (*Zea mays* L.), rye (*Secale cereale* L.), and pine (*Pinus sylvestris* L.), and with a second extract originating from corn pistils (*Zea mays* L.) and cytoplasm of pollen of corn (*Zea mays* L.), rye (*Secale cereale* L.), orchardgrass (*Dactylis glomerata* L.), and pine (*Pinus sylvestris* L.).

15. The method of claim 12, wherein the pharmaceutical product comprises an extract having:
    45% to 90% by weight of aqueous extract of cytoplasm of pollen from *Secale cereal* L. relative to the total weight of the extract;
    1% to 35% by weight of aqueous extract of cytoplasm of pollen from *Zea mays* L. relative to the total weight of the extract;
    0.01% to 5% by weight of aqueous extract of cytoplasm of pollen from *Pinus sylvestris* L. relative to the total weight of the extract;
    3% to 30% by weight of aqueous extract of cytoplasm of pollen from *Dactylis glomerata* L. relative to the total weight of the extract; and
    0.1% to 10% by weight of aqueous extract of pistil from *Zea mays* L. relative to the total weight of the extract.

16. An aqueous pollen and pistil extract obtained according to a process comprising:
    extracting a first aqueous extract of *Secale, Zea, Pinus sylvestris,* and *Dactylis* pollen in an aqueous medium comprising acetone, an alcohol, or a nonionic surfactant;
    extracting a second aqueous extract of *Zea mays* L. pollen and pistil in an aqueous medium comprising acetone, an alcohol, or a nonionic surfactant;
    spray-drying the first aqueous extract and the second aqueous extract;

recovering a powder comprising the pollen extract and pollen and pistil extract after spray-drying;

wherein the first aqueous extraction and the second aqueous extraction are performed at a temperature less than 45° C. with subsequent spray drying at a starting temperature in a range of 138° C. and 168° C., and a recovered pollen extract and pollen and pistil extract comprises beta-1,3-glucanase; and one or more of safranal, picrocrocin, and crocin, forming a tablet, capsule, or soft gel comprising the powder.

* * * * *